(12) United States Patent
Greenberg

(10) Patent No.: US 7,527,621 B2
(45) Date of Patent: *May 5, 2009

(54) IMPLANTABLE DRUG DELIVERY DEVICE

(75) Inventor: Robert Greenberg, Los Angeles, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 247 days.

This patent is subject to a terminal disclaimer.

(21) Appl. No.: 11/505,695

(22) Filed: Aug. 16, 2006

(65) Prior Publication Data

US 2007/0026048 A1    Feb. 1, 2007

Related U.S. Application Data

(60) Division of application No. 10/202,248, filed on Jul. 24, 2002, now Pat. No. 7,181,287, which is a continuation-in-part of application No. 09/783,236, filed on Feb. 13, 2001, now Pat. No. 7,338,522.

(51) Int. Cl.
*A61K 9/22* (2006.01)

(52) U.S. Cl. .................................. 604/890.1; 604/294

(58) Field of Classification Search ................ 604/289, 604/294–302, 521, 890.1–892.1, 288.01–288.04
See application file for complete search history.

(56) References Cited

U.S. PATENT DOCUMENTS

| | | | |
|---|---|---|---|
| 3,416,530 A | 12/1968 | Ness | |
| 3,618,604 A | 11/1971 | Ness | |
| 4,014,335 A | 3/1977 | Arnold | |
| 4,186,184 A * | 1/1980 | Zaffaroni | 424/427 |
| 4,573,481 A | 3/1986 | Bullara | |
| 4,628,933 A | 12/1986 | Michelson | |
| 4,969,468 A | 11/1990 | Byers | |
| 4,991,582 A | 2/1991 | Byers | |
| 5,098,443 A | 3/1992 | Parel | |
| 5,109,844 A | 5/1992 | de Juan | |
| 5,215,088 A | 6/1993 | Normann | |
| 5,378,475 A | 1/1995 | Smith | |
| 5,476,494 A | 12/1995 | Edell | |
| 5,750,926 A | 5/1998 | Schulman | |
| 5,797,898 A | 8/1998 | Santini | |
| 5,810,725 A | 9/1998 | Sugihara | |
| 5,904,144 A * | 5/1999 | Hammang et al. | 128/898 |
| 5,935,155 A | 8/1999 | Humayun | |
| 5,987,361 A | 11/1999 | Mortimer | |
| 6,123,861 A | 9/2000 | Santini | |
| 6,400,989 B1 | 6/2002 | Eckmiller | |
| 6,416,777 B1 * | 7/2002 | Yaacobi | 424/428 |
| 6,458,157 B1 | 10/2002 | Suaning | |

* cited by examiner

*Primary Examiner*—Nicholas D Lucchesi
*Assistant Examiner*—Nathan R Price
(74) *Attorney, Agent, or Firm*—Scott B. Dunbar; Gary D. Schnittgrund; Sumana Prabhu (57) ABSTRACT

The invention is directed to an implantable device to enable delivery of drugs to the retina. The device minimizes stress to the retina by virtue of its softness and smooth shape that conform to the retina. Drugs are delivered by osmosis or by the device dissolving. It may be connected to an externally mounted pump and drug reservoir that control the amount of drug. It contains one or more holes that are positioned to deliver drugs to the desired location. Drugs may stimulate the retina to enable vision in blind patients. Drugs may be injected directly inside the eye by a trans-scleral pump and valve drug delivery device.

6 Claims, 7 Drawing Sheets

IMPLANTABLE DRUG DELIVERY DEVICE

CROSS-REFERENCE TO RELATED APPLICATIONS

This patent application is a divisional application of U.S. patent application Ser. No. 10/202,248, filed Jul. 24, 2002, now U.S. Pat. No. 7,181,287 which is a continuation-in-part of U.S. patent application Ser. No. 09/783,236, filed on Feb. 13, 2001, now U.S. Pat. No. 7,338,522 entitled "IMPLANTABLE RETINAL ELECTRODE ARRAY CONFIGURATION FOR MINIMAL RETINAL DAMAGE AND METHOD OF REDUCING RETINAL STRESS." the disclosure of which is incorporated herein by reference.

GOVERNMENT RIGHTS NOTICE

This invention was made with government support under grant No. R24EY12893-01. The government has certain rights in the invention.

FIELD OF THE INVENTION

This invention relates to a device and methods and more particularly to a controlled time of release and rate of release, drug delivery device, which may be implanted in a living body.

BACKGROUND OF THE INVENTION

In 1755, LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthesis devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across neuronal membranes, which can initiate neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface. This placement must be mechanically stable, minimize the distance between the device electrodes and the neurons, and avoid undue compression of the neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 .mu.A current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. Such a device increases the possibility of retinal trauma by the use of its "bed of nails" type electrodes that impinge directly on the retinal tissue.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina.

The retina is extraordinarily fragile. In particular, retinal neurons are extremely sensitive to pressure; they will die if even a modest intraocular pressure is maintained for a prolonged period of time. Glaucoma, which is one of the leading causes of blindness in the world, can result from a chronic increase of intraocular pressure of only 10 mm Hg. Furthermore, the retina, if it is perforated or pulled, will tend to separate from the underlying epithelium, which will eventually render it functionless. Thus attachment of a conventional prosthetic retinal electrode device carries with it the risk of damage to the retina, because of the pressure that such a device could exert on the retina.

Byers, et al. received U.S. Pat. No. 4,969,468 in 1990 that disclosed a "bed of nails" electrode array that in combination with processing circuitry amplifies and analyzes the signal received from the tissue and/or which generates signals that are sent to the target tissue. The penetrating electrodes are damaging to the delicate retinal tissue of a human eye and therefore are not applicable to enabling sight in the blind.

In 1992, U.S. Pat. No. 5,109,844 issued to de Juan, et al. on a method of stimulating the retina to enable sight in the blind wherein a voltage stimulates electrodes that are in close proximity to the retinal ganglion cells. A planar ganglion cell-stimulating electrode is positioned on or above the retinal basement membrane to enable transmission of sight-creating stimuli to the retina. The electrode is a flat array containing 64 electrodes.

Norman, et al. received U.S. Pat. No. 5,215,088 in 1993 on a three-dimensional electrode device as a cortical implant for vision prosthesis. The device contains perhaps a hundred small pillars each of which penetrates the visual cortex in order to interface with neurons more effectively. The array is strong and rigid and may be made of glass and a semiconductor material.

U.S. Pat. No. 5,476,494, issued to Edell, et al. in 1995, describes a retinal array held gently against the retina by a cantilever, where the cantilever is anchored some distance from the array. Thus, the anchor point is removed from the area served by the array. This cantilever configuration introduces complexity and it is very difficult to control the restoring force of the cantilever due to varying eye sizes, which the instant invention avoids.

Sugihara, et al. received U.S. Pat. No. 5,810,725 in 1998 on a planar electrode to enable stimulation and recording of nerve cells. The electrode is made of a rigid glass substrate. The lead wires which contact the electrodes are indium tin oxide covered with a conducting metal and coated with platinum containing metal. The electrodes are indium tin oxide or a highly electrically conductive metal. Several lead-wire insulating materials are disclosed including resins.

U.S. Pat. No. 5,935,155, issued to Humayun, et al. in 1999, describes a visual prosthesis and method of using it. The Humayun patent includes a camera, signal processing electronics and a retinal electrode array. The retinal array is mounted inside the eye using tacks, magnets, or adhesives. Portions of the remaining parts may be mounted outside the eye. The Humayun patent describes attaching the array to the retina using retinal tacks and/or magnets. This patent does not address reduction of damage to the retina and surrounding tissue or problems caused by excessive pressure between the retinal electrode array and the retina.

Mortimer's U.S. Pat. No. 5,987,361 disclosed a flexible metal foil structure containing a series of precisely positioned holes that in turn define electrodes for neural stimulation of nerves with cuff electrodes. Silicone rubber may be used as the polymeric base layer. This electrode is for going around nerve bundles and not for planar stimulation.

An alternative approach to stimulating the retina with electrical stimulation is the stimulation of the retinal nerves with drugs.

Various drugs have been developed to assist in the treatment of a wide variety of ailments and diseases. However, in many instances such drugs are not capable of being administered either orally or intravenously without the risk of various detrimental side effects. Systems for administering such drugs have been developed, many of which provide a release rate that reduces the occurrence of detrimental side effects. For example, intravenous ganciclovir (GCV) is effective in the treatment of CMV retinitis in AIDS patients, but bone marrow toxicity limits its usefulness. It is further limited by the risk of sepsis related to permanent indwelling catheters and the inability to receive concurrent therapy with zidovudine (AZT).

One approach utilizes implantable microfluidic delivery systems, as the microchip drug delivery devices of Santini, et al. (U.S. Pat. No. 6,123,861) and Santini, et al. (U.S. Pat. No. 5,797,898) or fluid sampling devices, must be impermeable and they must be biocompatible. Greenberg, et al. in U.S. patent application Ser. No. 10/046,458 and Greenberg, et al. in U.S. patent application Ser. No. 10/096,183 present novel implantable microfluidic delivery systems for drugs and other materials, both of which are incorporated herein by reference in their entirety. The devices must not only exhibit the ability to resist the aggressive environment present in the body, but must also be compatible with both the living tissue and with the other materials of construction for the device itself. The materials are selected to avoid both galvanic and electrolytic corrosion.

In microchip drug delivery devices, the microchips control both the rate and time of release of multiple chemical substances and they control the release of a wide variety of molecules in either a continuous or a pulsed manner. A material that is impermeable to the drugs or other molecules to be delivered and that is impermeable to the surrounding fluids is used as the substrate. Reservoirs are etched into the substrate using either chemical etching or ion beam etching techniques that are well known in the field of microfabrication. Hundreds to thousands of reservoirs can be fabricated on a single microchip using these techniques.

The physical properties of the release system control the rate of release of the molecules, e.g., whether the drug is in a gel or a polymer form. The reservoirs may contain multiple drugs or other molecules in variable dosages. The filled reservoirs can be capped with materials either that degrade or that allow the molecules to diffuse passively out of the reservoir over time. They may be capped with materials that disintegrate upon application of an electric potential. Release from an active device can be controlled by a preprogrammed microprocessor, remote control, or by biosensor. Valves and pumps may also be used to control the release of the molecules.

A reservoir cap can enable passive timed release of molecules without requiring a power source, if the reservoir cap is made of materials that degrade or dissolve at a known rate or have a known permeability. The degradation, dissolution or diffusion characteristics of the cap material determine the time when release begins and perhaps the release rate.

Alternatively, the reservoir cap may enable active timed release of molecules, requiring a power source. In this case, the reservoir cap consists of a thin film of conductive material that is deposited over the reservoir, patterned to a desired geometry, and serves as an anode. Cathodes are also fabricated on the device with their size and placement determined by the device's application and method of electrical potential control. Known conductive materials that are capable of use in active timed-release devices that dissolve into solution or form soluble compounds or ions upon the application of an electric potential, including metals, such as copper, gold, silver, and zinc and some polymers.

When an electric potential is applied between an anode and cathode, the conductive material of the anode covering the reservoir oxidizes to form soluble compounds or ions that dissolve into solution, exposing the molecules to be delivered to the surrounding fluids. Alternatively, the application of an electric potential can be used to create changes in local pH near the anode reservoir cap to allow normally insoluble ions or oxidation products to become soluble. This allows the reservoir cap to dissolve and to expose the molecules to be released to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip.

One solution to achieving biocompatibility, impermeability, and galvanic and electrolytic compatibility for an implanted device is to encase the device in a protective environment. It is well known to encase implantable devices with glass or with a case of ceramic or metal. Schulman, et al. (U.S. Pat. No. 5,750,926) is one example of this technique. It is also known to use alumina as a case material for an implanted device as disclosed in U.S. Pat. No. 4,991,582. Santini, et al. (U.S. Pat. No. 6,123,861) discuss the technique of encapsulating a non-biocompatible material in a biocompatible material, such as poly(ethylene glycol) or polytetrafluoroethylene-like materials. They also disclose the use of silicon as a strong, non-degradable, easily etched substrate that is impermeable to the molecules to be delivered and to the surrounding living tissue. The use of silicon allows the well-developed fabrication techniques from the electronic microcircuit industry to be applied to these substrates. It is well known, however, that silicon is dissolved when implanted in living tissue or in saline solution.

An alternative approach to microfluidic devices is, for example, is an orally administered pill or capsule that contains a drug encapsulated within various layers of a composition that dissolves over a period of time in the digestive tract, thereby allowing a gradual or slow release of the drug into the system.

Another type of device for controlling the administration of such drugs is produced by coating a drug with a polymeric material permeable to the passage of the drug to obtain the desired effect. Such devices are particularly suitable for treating a patient at a specific local area without having to expose the patient's entire body to the drug. This is advantageous because any possible side effects of the drug could be minimized.

Such systems are particularly suitable for treating ailments affecting the eye. Advances for administering a drug to the external surface of the eye are disclosed in U.S. Pat. No. 4,014,335 to Arnold. Arnold describes various ocular inserts that act as a deposit or drug reservoir for slowly releasing a drug into the tear film for prolonged periods. These inserts are fabricated of a flexible polymeric material that is biologically inert, non-allergenic, and insoluble in tear fluid. To initiate the therapeutic programs of these devices, the ocular inserts are placed in the cul-de-sac between the sclera of the eyeball and the eyelid for administering the drug to the eye.

Devices formed of polymeric materials that are insoluble in tear fluid retain their shape and integrity during the course of the needed therapy to serve as a drug reservoir for continuously administering a drug to the eye and the surrounding tissues at a rate that is not effected by dissolution or erosion of the polymeric material. Upon termination of the desired therapeutic program, the device is removed from the cul-de-sac.

Another type of device used for sustained release of a drug to the external surface of the eye, described in U.S. Pat. No. 3,416,530, is manufactured with a plurality of capillary openings that communicate between the exterior of the device and the interior chamber generally defined from a polymeric membrane. While these capillary openings in this construction are effective for releasing certain drugs to the eye, they add considerable complexity to the manufacture of the device because it is difficult to control the size of these openings in large-scale manufacturing using various polymers.

Another device, described in U.S. Pat. No. 3,618,604, does not involve such capillary openings, but instead provides for the release of the drug by diffusion through a polymeric membrane. The device, in a preferred embodiment, as disclosed in that patent, comprises a sealed container having the drug in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

Another such device, described in U.S. Pat. No. 4,014,335, comprises a three-layered laminant having a pair of separate and discrete first and third walls formed of a material insoluble in tear fluid with one of the walls formed of a drug release material permeable to the passage of drug and the other wall formed of a material impermeable to the passage of the drug.

Smith, U.S. Pat. No. 5,378,475, discusses sustained release drug delivery devices for selected areas wherein release of the drug is allowed to pass through the device in a controlled manner by using permeable coatings. Parel, U.S. Pat. No. 5,098,443, describes methods of implanting intraocular and intraorbital devices for controlled release of drugs as a polymer biodegrades or as the implant releases the drug by osmosis.

The above described systems and devices are intended to provide sustained release of drugs effective in treating patients at a desired local or systemic level for obtaining certain physiological or pharmacological effects. However, there are many disadvantages associated with their use including the fact that it is often difficult to obtain the desired release rate of the drug. The need for a better release system is especially significant in the treatment of CMV retinitus.

Further situations that would benefit from an improved drug delivery device for interior of an eye include neurotrophic factors, anti-inflammatory, anti-angiogenic (e.g., anti-vegf) anti-viral, anti-bacterial, and anti-neoplastic (i.e., anti cancer) drugs. These various treatments would benefit blindness, caused for example by outer retinal blindness, glaucoma, macular degeneration, diabetic retinopthaly, and reininitis uveitis, to name a few. Thus, there remains a long-felt need in the art for an improved system for providing sustained release of a drug to a patient to obtain a desired local or systemic physiological or pharmacological effect. In addition, all of these devices release their drug into the tear film. If relatively high levels are required inside the eye, such devices are ineffective.

OBJECTS OF THE INVENTION

It is an object of the invention to attach an electrode array body to the retina of an eye and enable blind people to see images.

It is an object of the invention to attach an electrode array body to the retina while avoiding or minimizing harmful stresses on the retina from the electrode array body.

It is an object of the invention to enable a surgeon to easily locate the mounting aperture for attachment of an electrode array body to the retina of an eye by a surgical tack.

It is an object of the invention to provide tabs for attachment of the electronics and feeder cable to the recipient of the retinal electrode array.

It is an object of the invention to provide drugs to the interior of an eye by an implanted device.

It is an object of the invention to enable vision by stimulating the retina with drugs that are injected on the retina with an implanted device.

Other objects, advantages and novel features of the present invention will become apparent from the following detailed description of the invention when considered in conjunction with the accompanying drawing.

DETAILED DESCRIPTION OF THE PREFERRED EMBODIMENTS

The following description is the best mode presently contemplated for carrying out the invention. This description is not to be taken in a limiting sense, but is made merely for describing the general principles of the invention. The scope of the invention should be determined with reference to the claims.

Figure 1:
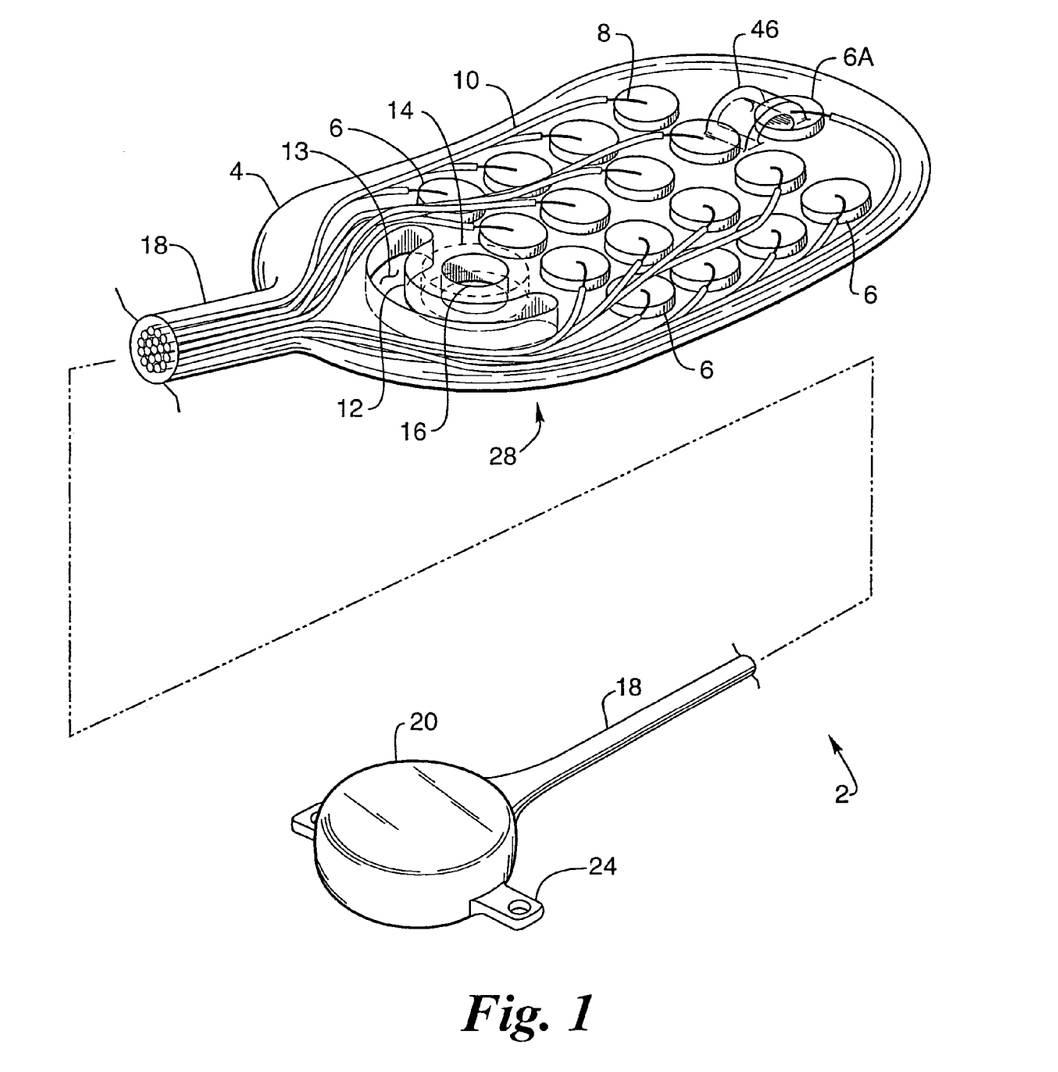
FIG. 1 illustrates a perspective view of the retinal electrode array assembly showing the electrodes and signal conductors as well as mounting aperture for tacking the assembly inside the eye, wherein both the array and its associated electronics are located inside the eye.

FIG. 1 provides a perspective view of a preferred embodiment of the retinal electrode array, generally designated 2, comprising oval-shaped electrode array body 4, a plurality of electrodes 6 made of a conductive material, such as platinum or one of its alloys, but that can be made of any conductive biocompatible material such as iridium, iridium oxide or titanium nitride, and single reference electrode 6A made of the same material as electrode 6, wherein the electrodes are individually attached to separate conductors 8 made of a conductive material, such as platinum or one of its alloys, but which could be made of any biocompatible conductive material, that is enveloped within an insulating sheath 10, that is preferably silicone, that carries an electrical signal to each of the electrodes 6. "Oval-shaped" electrode array body means that the body may approximate either a square or a rectangle shape, but where the corners are rounded. The reference electrode 6A is not necessarily stimulated, but is attached to a conductor, as are electrodes 6. The electrodes could be used in another application as sensors to transmit electrical signals from a nerve. The electrodes 6 transmit an electrical signal to the eye while reference electrode 6A may be used as a ground, reference, or control voltage.

Electrode array body 4 is made of a soft material that is compatible with the body. In a preferred embodiment, array body 4 is made of silicone having a hardness of about 50 or less on the Shore A scale as measured with a durometer. In an alternate embodiment, the hardness is about 25 or less on the Shore A scale as measured with a durometer. It is a substantial goal to have electrode array body 4 in intimate contact with the retina of the eye.

Strain relief internal tab 12, defined by a strain relief slot 13 that passes through the array body 4, contains a mounting aperture 16 for fixation of the electrode array body 4 to the retina of the eye by use of a surgical tack, although alternate means of attachment such as glue or magnets may be used. Reinforcing ring 14 is colored and opaque to facilitate locating mounting aperture 16 during surgery and may be made of tougher material, such as high toughness silicone, than the body of the electrode array body to guard against tearing.

Signal conductors 8 are located in an insulated flexible feeder cable 18 carrying electrical impulses from the electronics 20 to the electrodes 6, although the electrodes can be sensors that carry a signal back to the electronics. Signal conductors 8 can be wires, as shown, or in an alternative embodiment, a thin electrically conductive film, such as platinum, deposited by sputtering or an alternative thin film deposition method. In a preferred embodiment, the entire retinal electrode array 2 including the feeder cable 18 and electronics 6 are all implanted inside the eye. Electronics 20 may be fixated inside the eye to the sclera by sutures or staples that pass through fixation tabs 24. The conductors are covered with silicone insulation.

Grasping handle 46 is located on the surface of electrode array body 4 to enable its placement by a surgeon using forceps or by placing a surgical tool into the hole formed by grasping handle 46. Grasping handle 46 avoids damage to the electrode body that might be caused by the surgeon grasping the electrode body directly. Grasping handle 46 also minimizes trauma and stress-related damage to the eye during surgical implantation by providing the surgeon a convenient method of manipulating electrode array body 4.

Grasping handle 46 is made of silicone having a hardness of about 50 on the Shore A scale as measured with a durometer. A preferred embodiment of the electrode array body 4 is made of a very soft silicone having hardness of 50 or less on the Shore A scale as measured with a durometer. The reinforcing ring 14 is made of opaque silicone having a hardness of 50 on the Shore A scale as measured with a durometer.

Figure 2:
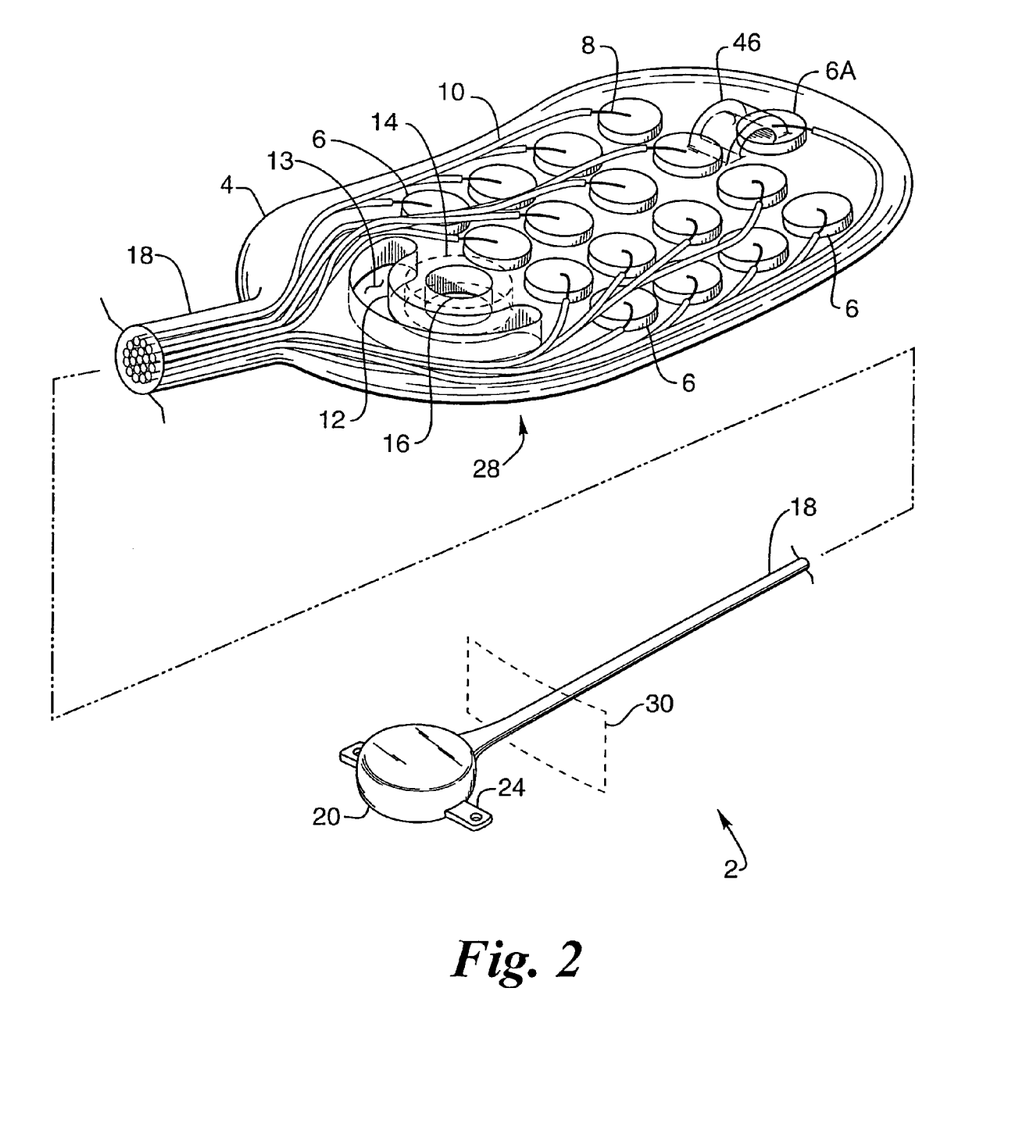
FIG. 2 illustrates a perspective view of the retinal electrode array assembly showing the electrodes and signal conductors as well as mounting aperture for tacking the assembly inside the eye, wherein the associated electronics are located outside the eye.

FIG. 2 provides a perspective view of the retinal electrode array 2 wherein the electrode array body 4 is implanted inside the eye and the electronics 20 are placed outside the eye with the feeder cable 18 passing through sclera 30. In this embodiment, electronics 38 are attached by fixation tabs 24 outside the eye to sclera 30.

Figure 3:
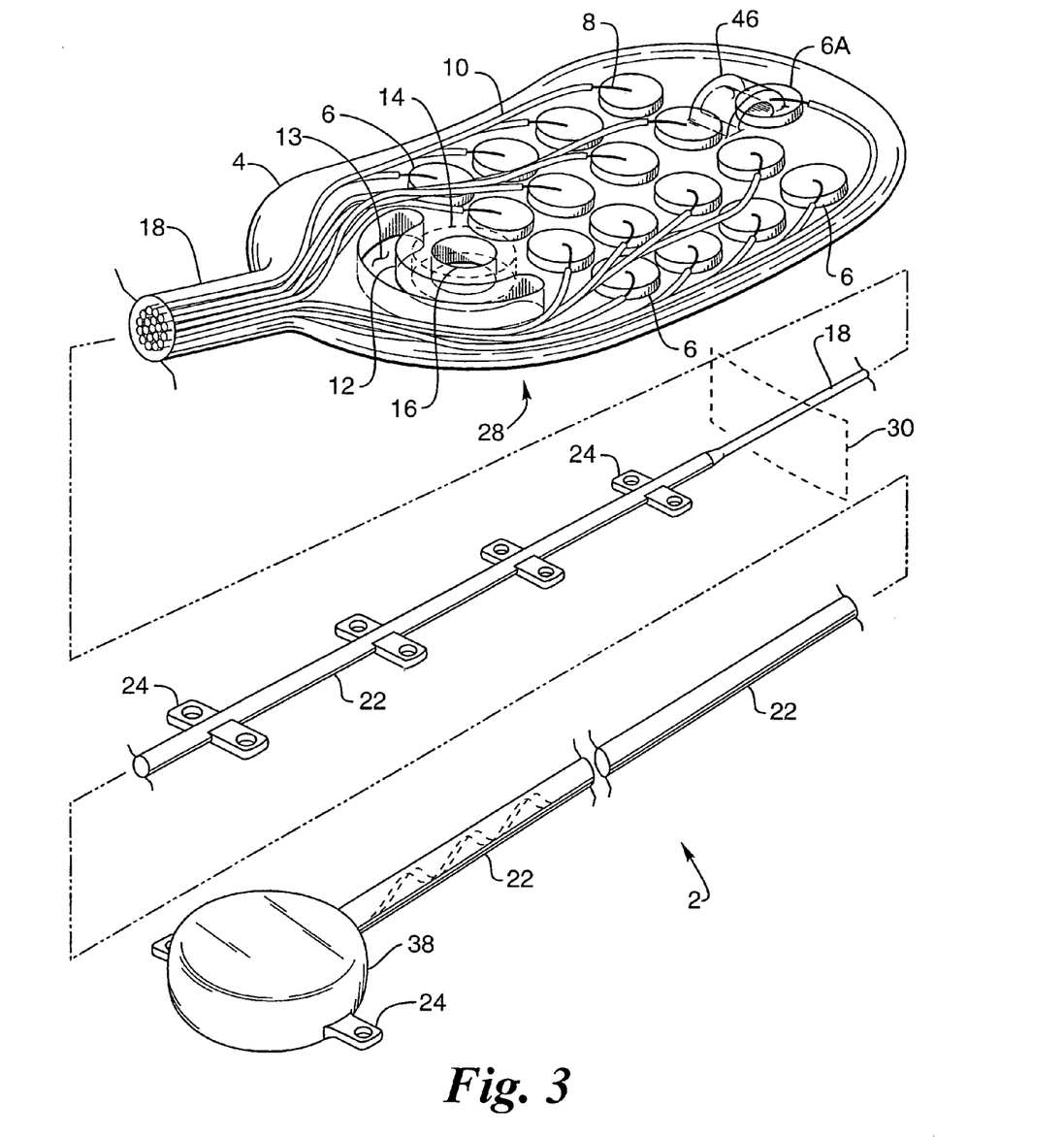
FIG. 3 illustrates a perspective view of the retinal electrode array assembly wherein the array is installed inside the eye and the associated electronics are installed outside the eye at some distance from the sclera wherein the feeder cable contains both a coiled cable leading between the electronics and the sclera and a series of fixation tabs along the feeder cable for securing the feeder cable by suture.

FIG. 3 provides a perspective view of retinal electrode array 2 wherein electrode array body 4 is implanted on the retina inside the eye and electronics 38 are placed outside the eye some distance from sclera 30 wherein feeder cable 18 contains sheathed conductors 10 as silicone-filled coiled cable 22 for stress relief and flexibility between electronics 38 and electrode array body 4. Feeder cable 18 passes through sclera 30 and contains a series of fixation tabs 24 outside the eye and along feeder cable 18 for feeder cable 18 to sclera 30 or elsewhere on the recipient subject.

Figure 4:
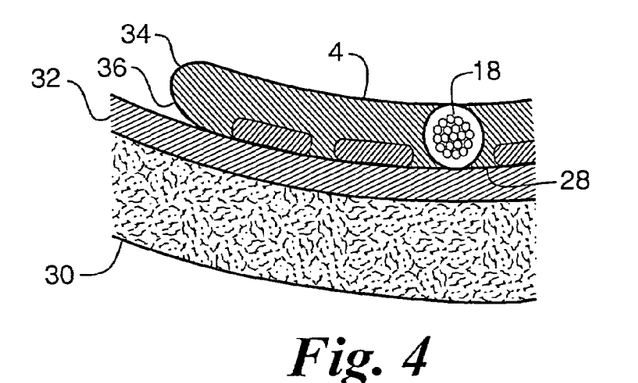
FIG. 4 depicts a cross-sectional view of the retinal electrode array, the sclera, the retina and the retinal electrode array showing the electrodes in contact with the retina.

FIG. 4 provides a cross-sectional view of electrode array body 4 in intimate contact with retina 32. The surface of electrode array body 4 in contact with retina 32 is a curved surface 28 substantially conforming to the spherical curvature of retina 32 to minimize stress concentrations therein. Further, the decreasing radius of spherical curvature of electrode array body 4 near its edge forms edge relief 36 that causes the edges of array body 4 to lift off the surface of retina 32 eliminating stress concentrations. The edge of electrode array body 4 has a rounded edge 34 eliminating stress and cutting of retina 32. The axis of feeder cable 18 is at right angles to the plane of this cross-sectional view. Feeder cable 18 is covered with silicone.

Figure 5:
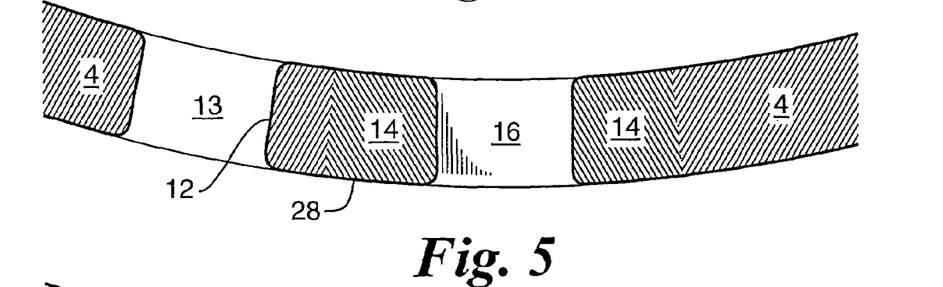
FIG. 5 depicts a cross-sectional view of the retinal electrode array showing a strain relief slot, strain relief internal tab and a mounting aperture through a reinforcing ring for a mounting tack to hold the array in position.

FIG. 5 provides a cross-sectional view of electrode array body 4 showing spherically curved surface 28, strain relief slot 13 and mounting aperture 16 through which a tack passes to hold array body 4 in intimate contact with the eye. Mounting aperture 16 is located in the center of reinforcing ring 14 that is opaque and colored differently from the remainder of array body 4, making mounting aperture 16 visible to the surgeon. Reinforcing ring 14 is made of a strong material such as tough silicone, which also resists tearing during and after surgery. Strain relief slot 13 forms strain relief internal tab 12 in which reinforcing ring 14 is located. Stresses that would otherwise arise in the eye from tacking array body 4 to the eye through mounting aperture 16 are relieved by virtue of the tack being located on strain relief internal tab 12.

Figure 6:
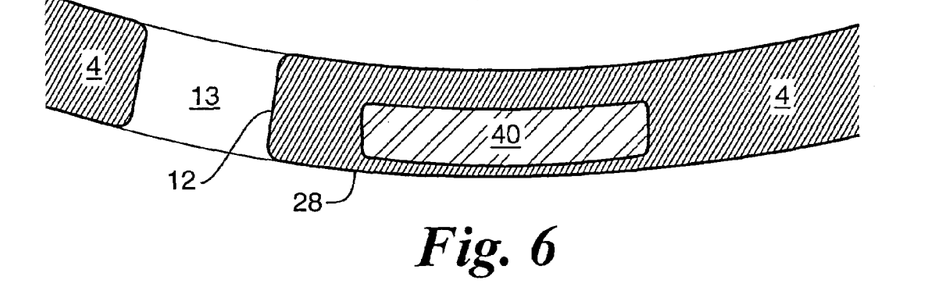
FIG. 6 illustrates a cross-sectional view of the retinal electrode array showing a strain relief slot and a ferromagnetic keeper to hold the array in position.

FIG. 6 provides a cross-sectional view of a preferred embodiment of electrode array body 4 showing ferromagnetic keeper 40 that holds electrode array body 4 in position against the retina by virtue of an attractive force between ferromagnetic keeper 40 and a magnet located on and attached to the eye.

Figure 7:
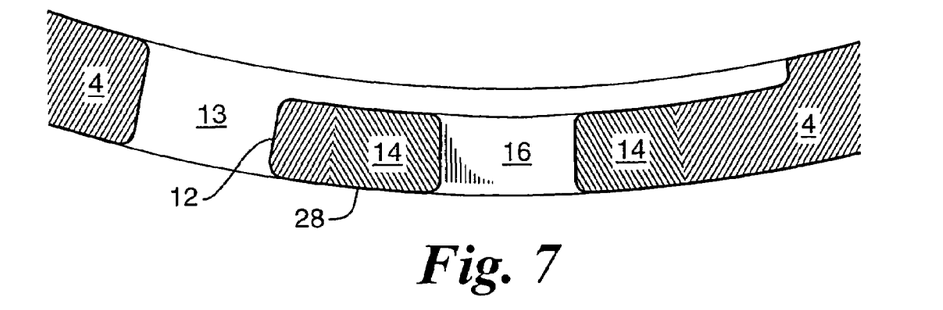
FIG. 7 illustrates a cross-sectional view of the retinal electrode array showing a strain relief slot and a mounting aperture through a reinforcing ring for a mounting tack to hold the array in position, wherein the strain relief internal tab containing the mounting aperture is thinner than the rest of the array.

FIG. 7 is a cross-sectional view of the electrode array body 4 wherein internal tab 12 is thinner than the rest of electrode array body 4, making this section more flexible and less likely to transmit attachment induced stresses to the retina. This embodiment allows greater pressure between array body 4 and the retina at the point of attachment, and a lesser pressure at other locations on array body 4, thus reducing stress concentrations and irritation and damage to the retina.

A significant feature of this drug delivery device is that the drug delivery device is located out of the field of vision and does not block light that is passing from the lens to the retina. Further, the device is securely mounted to the retina at a desired location without damaging the retina. Further, a preferred embodiment is presented in FIG. 8, which provides a cross-section through an eye 101 of a passive drug-delivery device, wherein the lens 131 and retina 132 are indicated. The drug-containing pillow 107 is preferably securely attached to the retina 132 by tack 103.

In alternate embodiments, the drug-containing pillow 107 may be located elsewhere in the living body, such as in an ear or attached to an eardrum.

Figure 8:
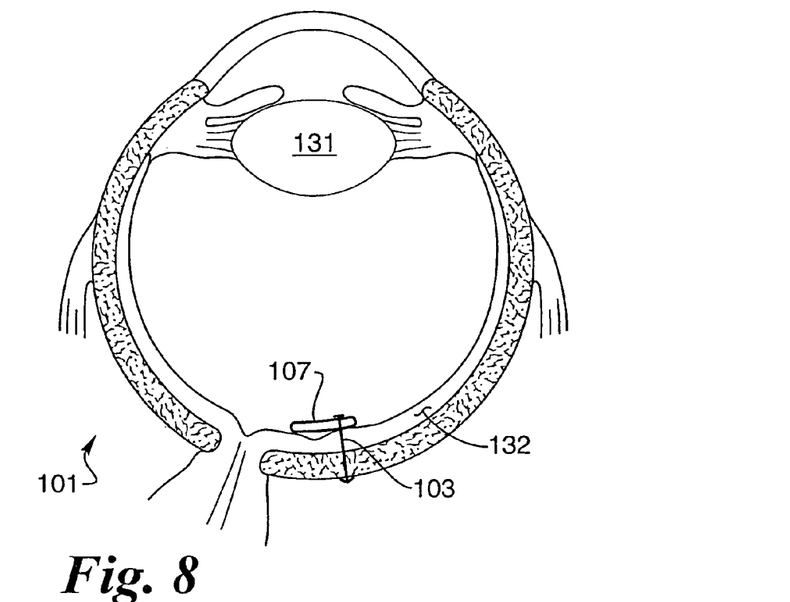
FIG. 8 illustrates a cross-sectional view of an eye showing an array body attached to a retina.

In accordance with a significant feature of this preferred embodiment, the pillow 107 may be formed from biodegradable materials, such as polymers, to release a drug as the material, preferably a polymer, biodegrades. In an alternative embodiment, the pillow 107 may be in the form of a hollow flexible polymeric cocoon with the drug disposed therewithin for slow release by osmosis. As a further alternative embodiment, the drug may be embedded in the body of the pillow 107, such that the drug is slowly released by osmosis while leaving the pillow 107 substantially intact, such that the pillow 107 may be removed surgically. Attachment of the drug-containing pillow 107 to the retina has the significant benefit of placing controlled and concentrated amounts of drugs precisely where they are needed to optimize the therapeutic benefit. The physical shape of pillow 107 and its method of attachment are optimized to eliminate or minimize physical stress on the retina and the associated eye structures to avoid permanent damage to the eye.

Figure 9:
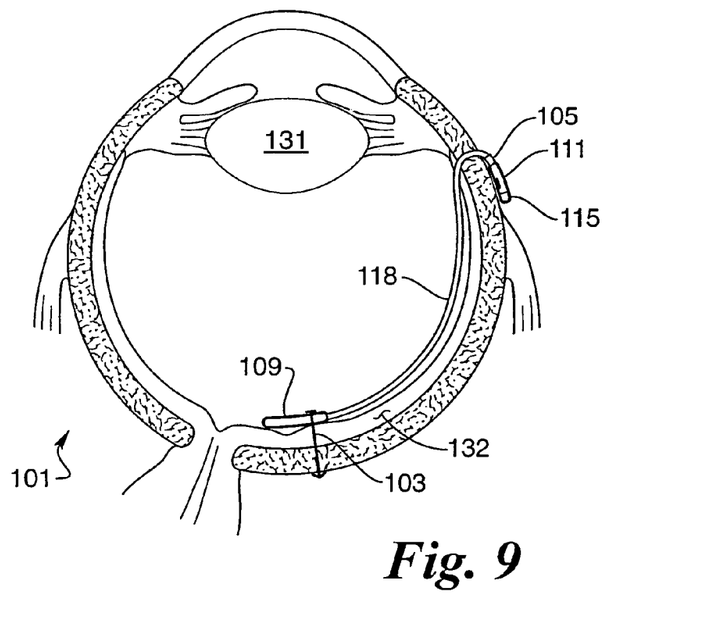
FIG. 9 illustrates a cross-sectional view of an eye showing an array body with external reservoir.

In contrast to the passive drug delivery device of FIG. 8, and in accordance with a further preferred embodiment of the present invention, FIG. 9 provides a cross-section through an eye 101, as previously presented in FIG. 8, with an active drug delivery device 109 preferably securely attached by tack 103 to the retina 132. Delivery device 109 receives drugs from reservoir 111. The drugs are transferred by pressure development device 115 through feeder tube 118. The flow rate is preferably controlled in part by micro-valve 105, which is located external to the eye, and is preferably co-located outside the eye with the reservoir 111 and pressure development device 115. The reservoir 111, pressure development device 115 and valve 105 are preferably attached to the sclera on the outside of the eye, preferably under the conjunctiva, to enable repair, replacement, and/or refilling the drug delivery device.

In an alternate embodiment, drug delivery device 109 may be located elsewhere in the living body, such as in an ear or on an eardrum.

Figure 10:
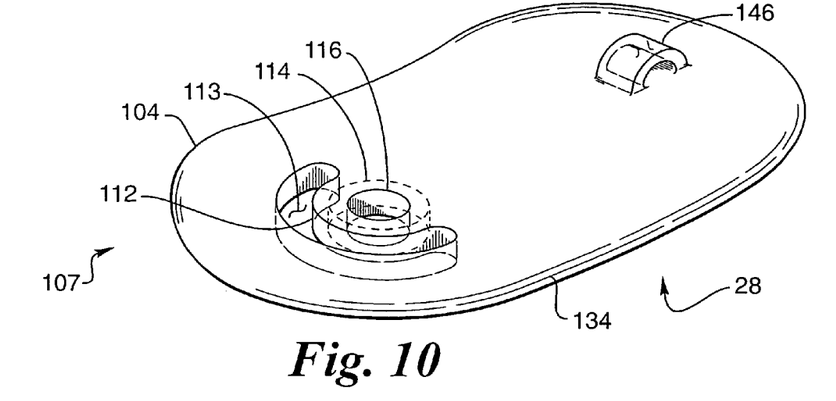
FIG. 10 illustrates a perspective view of an array body.

FIG. 10 provides a perspective view of a preferred embodiment of the pillow, generally designated 107, and previously presented in FIG. 8 comprising oval-shaped pillow 107. "Oval-shaped" pillow 107 means that the body may approximate either a square or a rectangle shape, but where the corners are rounded, as with rounded edge 134.

Pillow 107 is made of a soft material that is compatible with the body. In a preferred embodiment, pillow 107 is made of a polymer having a hardness of about 50 or less on the Shore A scale, as measured with a durometer. In an alternate embodiment, the hardness is about 25 or less on the Shore A scale, as measured with a durometer. It is a substantial goal to have pillow 107 in intimate contact with the retina 132 of the eye.

Strain relief internal tab 112, defined by a strain relief slot 113 that passes through the pillow 107, contains a mounting aperture 116 for fixation of the pillow 107 to the retina 132 of the eye by use of a surgical tack 103, although alternate means of attachment such as glue or magnets may be used. Reinforcing ring 114 is colored and opaque to facilitate locating mounting aperture 116 during surgery and may be made of tougher material, such as high toughness polymer, than the body of the pillow 107, to guard against tearing.

Grasping handle 146 is located on the surface of pillow 107 to enable its placement by a surgeon using forceps or by placing a surgical tool into the hole formed by grasping handle 146. Grasping handle 146 avoids damage to the pillow 107 that might be caused by the surgeon grasping the body directly. Grasping handle 146 also minimizes trauma and stress-related damage to the eye during surgical implantation by providing the surgeon a convenient method of manipulating pillow 107. Grasping handle 146 is preferably made of a material, such as a polymer, having a hardness of about 50 on the Shore A scale, as measured with a durometer.

Figure 11:
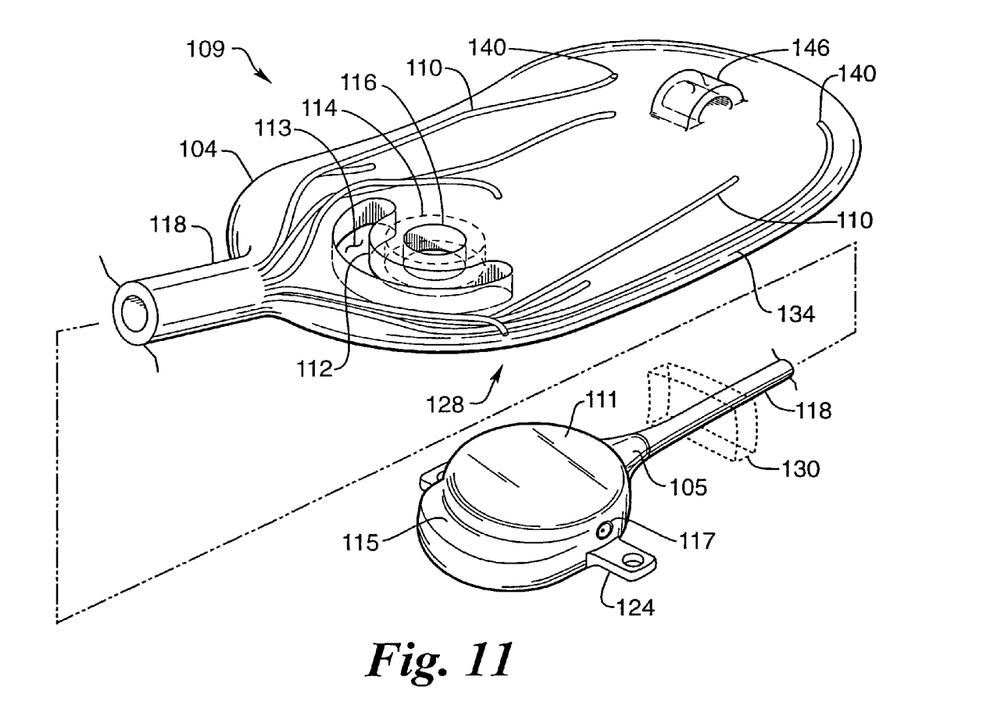
FIG. 11 illustrates a perspective view of an array body with an attached reservoir.

FIG. 11 provides a perspective view of a preferred embodiment of the present invention, as previously presented in FIG. 9, comprising delivery device 109 that is connected by feeder tube 118 to drug reservoir 111 and pressure development device 115. It is obvious that pressure development device 115 may equally well be replaced by any of a number of known methods of delivering a fluid from the reservoir 111 and along the tube 118. As previously discussed, the reservoir 111 is preferably mounted outside the eye to the sclera, preferably under the conjunctiva, by fixation tabs 124. The feeder tube 118 passes through an incision in the sclera 130. In accordance with a significant feature of this preferred embodiment, a micro-valve 105 is located in feeder tube 118 outside the eye. Together with pressure development device 115, preferably a micro-pump, this valve 105 controls the flow of drugs to the delivery device 109.

In a preferred environment, feeder tube 118 branches into a plurality of tubes 110 in delivery device 109. Each tube 110 then creates a capillary opening 140 where it breaches the surface of delivery device 109. While FIG. 11 shows the capillary openings 140 located on the top, bottom and sides of delivery device 109, it is obvious that the tubes may be placed where desired in order to maximize the benefit of the drug. In an exemplary design, therefore, all of the capillary openings 140 are located on the bottom of delivery device 109, for example, when it is desirable to deliver the drug to a local point on the retina. In a further exemplary design, only one capillary opening 140 may be located to place the drug at a single location on the retina, for example.

A significant feature of this preferred embodiment is that with an externally mounted reservoir 111 the reservoir 111 may be refilled by injecting additional drug into refill aperture 117.

In accordance with a further significant feature of a preferred embodiment of this invention, the stresses that are generated when delivery device 109 contacts the retina are minimized, as previously discussed, by using an oval shaped design with stress concentrations eliminated or minimized by using soft polymers and rounded edges. For example, the "oval-shaped" delivery device 109 means that the body may approximate either a square or a rectangle shape, but where delivery device 109 is comprised of rounded edges 134.

Delivery device 109 is made of a soft material that is compatible with the body. In a preferred embodiment, delivery device 109 is made of a polymer having a hardness of about 50 or less on the Shore A scale, as measured with a durometer. In an alternate embodiment, the hardness is about 25 or less on the Shore A scale, as measured with a durometer. It is a substantial goal to have delivery device 109 in intimate contact with the retina 132 of the eye.

Strain relief internal tab 112, defined by a strain relief slot 113 that passes through the delivery device 109, contains a mounting aperture 116 for fixation of the delivery device 109 to the retina 132 of the eye by use of a surgical tack 103, although alternate means of attachment such as glue or magnets may be used. Reinforcing ring 114 is colored and opaque to facilitate locating mounting aperture 116 during surgery, and may be made of tougher material, such as high toughness polymer, than the body of the delivery device 109, to guard against tearing.

Grasping handle 146 is located on the surface of delivery device 109 to enable its placement by a surgeon using forceps or by placing a surgical tool into the hole formed by grasping handle 146. Grasping handle 146 avoids damage to the delivery device 109 that might be caused by the surgeon grasping the body directly. Grasping handle 146 also minimizes trauma and stress-related damage to the eye during surgical implantation by providing the surgeon a convenient method of manipulating pillow 107. Grasping handle 146 is made of a polymer having a hardness of about 50 on the Shore A scale, as measured with a durometer.

Figures 12, 13:
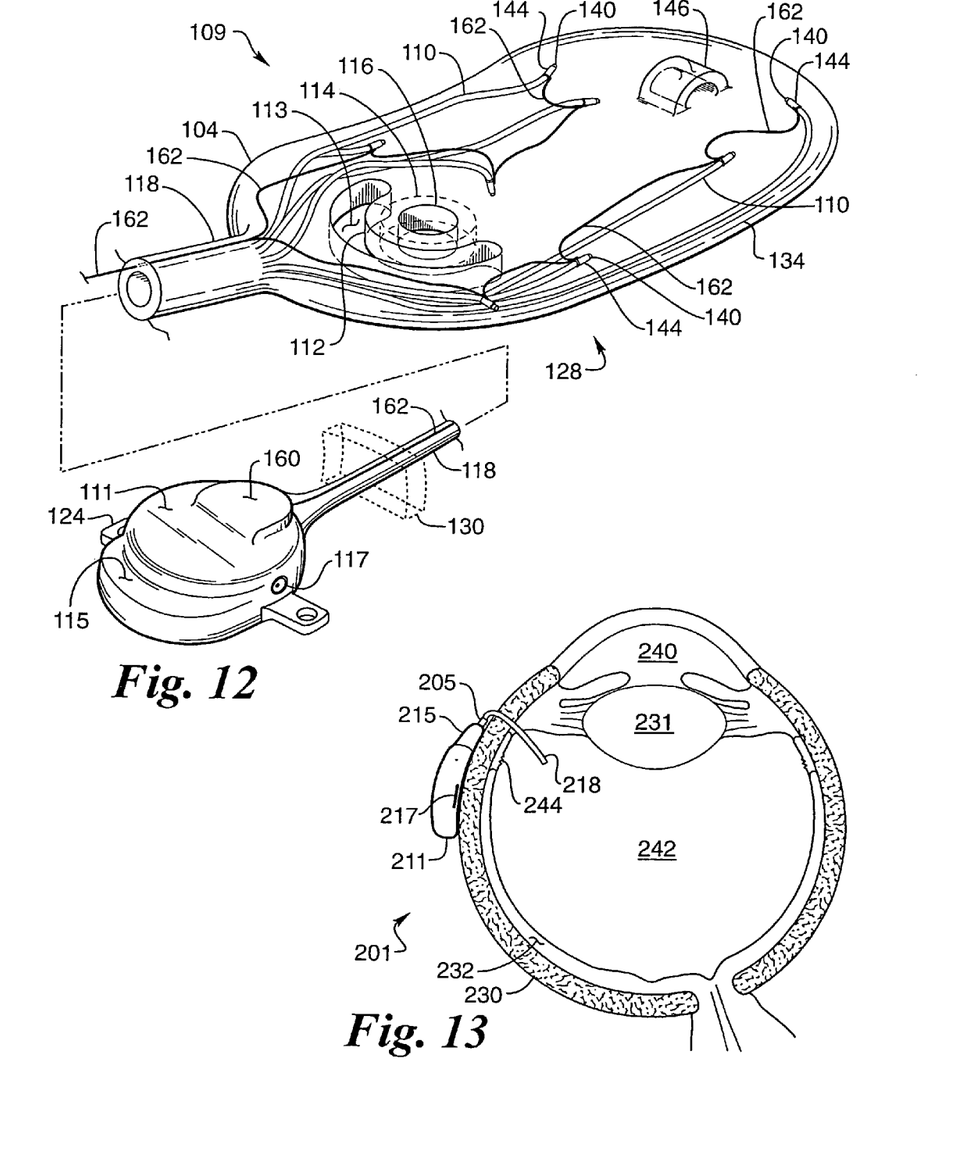
FIG. 12 illustrates a perspective view of a multi-reservoir array body with an attached reservoir.
FIG. 13 illustrates a cross-sectional view of an eye showing a drug delivery system.

FIG. 12 provides a perspective view of a preferred embodiment of the present invention comprising delivery device 109 that is connected by feeder tube 118 to drug reservoir 111 and pressure development device 115. It is obvious that pressure development device 115 may equally well be replaced by any of a number of known methods of delivering a fluid from the reservoir 111 and along the tube 118. The reservoir 111 is preferably mounted outside the eye to the sclera by fixation tabs 124. The feeder tube 118 passes through an incision in the sclera 130.

In accordance with a significant feature of this preferred embodiment, at least one micro-valve 144 is located in each feeder tube 118. Preferably, the micro-valve is located near capillary opening 140, which is in delivery device 109. Together with pressure development device 115, the valves 144 control the flow of drugs. Each micro-valve 144 is connected to a control wire 162 that in turn is connected to a controller 160. It is preferred that only one wire or set of wires be utilized to control the micro-valves 144, if more than one micro-valve 144 controlled capillary opening 140 is present. In this multiplex control scheme, digital signals from controller 160 control each micro-valve 144 independently of all other micro-valves 144. In a preferred embodiment, controller 160 is located external to the eye near reservoir 111.

In a preferred environment, feeder tube 118 branches into a plurality of tubes 110 in delivery device 109. Each tube 110 then creates a capillary opening 140 where it breaches the surface of delivery device 109. While FIG. 12 shows the capillary openings 140 located on the top, bottom and sides of delivery device 109, it is obvious that the tubes may be placed where desired in order to maximize the benefit of the drug.

A further alternative embodiment, not fully illustrated but a variant of representation of FIG. 12, places the tubes 110 and their capillary openings 140 in a preferably symmetrical array located between grasping handle 146 and aperture 116. An exemplary array is an equidistance 4.times.4 array, wherein the sixteen capillary openings 140 are all located on the curved surface 128, such that the neurotransmitter drug is released adjacent to the retina. One known example of such a drug includes glutamate. There may be a plurality of different drugs used to stimulate the eye in order to achieve vision, and that each drug may be associated with an independent reservoir 111 and tube 110 which in turn has an independent capillary opening 140. This use of multiple drugs, not illustrated, would enable the retina to be stimulated to achieve color vision, for example, by the controlled use of independent color-stimulating drugs or mixtures of drugs.

In an alternate embodiment, the neurotransmitter drug may be delivered to neural tissue to stimulate vision, when delivery device 109 is placed on select neural tissue instead of on the retina of an eye.

A further alternative embodiment is represented in FIG. 13, where the eye 201 is shown in cross-section and the lens 231 and retina 232 are delineated. The drug or drugs to be delivered are contained in externally mounted reservoir 211, which is preferably located near a pressure delivery source, such as the pressure development device 215, which may be a micro-pump, for example. The reservoir 211 can be refilled through refill aperture 217 by injection, for example. A preferred material for the refill aperture 217 is silicone. A microvalve 205 is controlled by a controller to allow the drug to pass along feeder tube 218. Feeder tube 218 passes through an incision in the sclera 230 and terminates in a preferred location within eye 201. A preferred location for the incision is in the pars plana 244.

The preferred location for terminating the feeder tube 218 for drug delivery may be in the vitreous 242 or in the anterior chamber 240. If in the anterior chamber 240, the feeder tube 218 looks much like a glaucoma drain, for example. Drugs may be delivered in controlled doses to the precise area of the eye 201 desired to optimize the therapeutic effect of treatment with minimal drug usage.

Obviously, many modifications and variations of the present invention are possible in light of the above teachings. It is therefore to be understood that within the scope of the appended claims, the invention may be practiced otherwise than as specifically described.

The invention claimed is:

1. An implantable device for drug delivery comprising:
a biologically inert hollow body defining at least one void;
said void containing at least one drug;
said hollow body having a generally oval shape;
said oval shaped body being curved such that it substantially conforms to the spherical curvature of at least a portion of a recipient's eye,
said oval shape being optimized to minimize physical stress on the retina;
said inert body further comprising at least one mounting aperture suitable for attaching said inert body to a retina with a tack and
said inert body further comprising a strain relief tab which is thinner than the rest of said inert body, defined by a strain relief slot partially around said mounting aperture.

2. The implantable device for drug delivery according to claim 1, wherein said drug delivery is comprised of osmotic release.

3. The implantable device for drug delivery according to claim 1, wherein said generally oval shape is generally circular.

4. The implantable device for drug delivery according to claim 1, wherein said inert body is comprised of an oval shape having a radius of spherical curvature that approximates the curvature of the eye, that is decreasing near the edge of said inert body, thus causing the edge of said inert body to lift off of the retina, eliminating stress concentrations in the retina from contact with said inert body.

5. The implantable device for drug delivery according to claim 1, wherein said inert body is attached to a grasping handle that is suitable for holding with a surgical instrument during implantation.

6. The implantable device for drug delivery according to claim 1, wherein the drug delivery is neurotrophic factor.

* * * * *